United States Patent [19]
Lorens et al.

[11] Patent Number: 5,955,508
[45] Date of Patent: *Sep. 21, 1999

[54] METHOD FOR THE ENHANCEMENT OF LYMPHOCYTE ACTIVITY AGAINST OPPORTUNISTIC MICROBIAL PATHOGENS

[75] Inventors: Stanley A. Lorens, Forest Park; Herbert L. Mathews, Elmhurst; John Clancy, Jr., Naperville; Joanna Goral, Woodridge, all of Ill.; Brigitte Riveline, Paris, France

[73] Assignee: Loyola University of Chicago, Maywood, Ill.

[*] Notice: This patent issued on a continued prosecution application filed under 37 CFR 1.53(d), and is subject to the twenty year patent term provisions of 35 U.S.C. 154(a)(2).

[21] Appl. No.: 08/729,868

[22] Filed: Oct. 15, 1996

[51] Int. Cl.$^6$ .................................................. A61K 31/135
[52] U.S. Cl. ........................................... 514/649; 514/654
[58] Field of Search ...................................... 514/649, 654

[56] References Cited

U.S. PATENT DOCUMENTS

| | | | |
|---|---|---|---|
| 4,309,445 | 1/1982 | Wurtman | 424/325 |
| 5,502,080 | 3/1996 | Hitzig | 514/654 |

FOREIGN PATENT DOCUMENTS

2663539  12/1991  France .

OTHER PUBLICATIONS

Merck Manual, 14th Ed, 1982 pp. 155, 298, 1625, 1626.
Clancy et al, 1991, Int J. Immunopharmac. vol. 13 #8 pp. 1203–1212.
Hadden, John W., "Immunostimulants", TIPS 14, pp. 169–174 (1993).
Hadden, John W., "The Immunotherapy of HIV Infection With Drugs", Immunology of HIV Infection, edited by Sudhir Gupta, Plenum Press, New York, pp. 475–491 (1996).
Hadden, John W., "Immunotherapy of human immunodeficiency virus infection", TIPS Reviews 12, pp. 107–111 (1991).
Kirkpatrick et al., "Host factors in defense against fungal infections", American Journal of Medicine 77 4(D), pp. 1–12 (1984) (Abstract only).
Romani et al., "Initiation of T–helper cell immunity to *Candida albicans* by IL–12: the role of neutrophils", Chemical Immunology 68, pp. 110–135 (1997) (Original Abstract plus retyped copy of same).
Beno, David W. A. and Mathews, Herbert L., "Quantitative measurement of lymphocyte mediated growth inhibition of *Candida albicans* ", Journal of Immunological Methods 164, pp. 155–164 (1993).
Beno et al., "Growth Inhibition of *Candida albicans* Hyphae by CD8+ Lymphocytes", J. Immunol. 54, pp. 5273–5281 (1995).

Blanchard et al., "Production of Granulocyte–Macrophage Colony–Stimulating Factor by Large Granular Lymphocytes Stimulated with *Candida Albicans*: Role in Activation of Human Neutrophil Function", Blood 77, pp. 2259–2265 (1991).
Arancia et al., "Noninhibitory Binding of Human Interleukin–2–Activated Natural Killer Cells to the Germ Tube Forms of *Candida albicans*", Infection and Immunity 63, pp. 280–288 (1995).
1992 Merck Manual (16th Edition) pp. 166–167, 266–267, 2422–2423.
Lancet 337:1315–1316 (1991).
Clancy and Lorens in Behavioral Brain Research 73:355–358 (1996).
Clancy, J., Jr. et al.. 1993. Interactions between serotonin and the immune system: an overview. In: P.M. Vanhoutte et al., (Eds.), Serotonin From Cell Biology to Pharmacology and Therapeutics. Kluwer: London, pp. 353–357.
Lorens, S.A., et al.. 1993. The stimulatory effects of d–fenfluramine (d–FEN) on blood and spleen immune functions in the Fischer 344 rat are age and sex dependent. In: P.M. Vanhoutte et al. (Eds.), Serotonin From Cell Biology to Pharmacology and Therapeutics. Kluwer: London, pp. 337–343.
Petrovic, L.M., et al. 1991. Subchronic d–Fenfluramine treatment enhances the immunological competence of old female Fischer 344 rats. In: J.R. Fozard and P.R. Saxena (Eds.), Serotonin: Molecular Biology, Receptors and Functional Effects. Birkhauser Verlag: Basel, pp. 389–397.
Clancy, J., Jr., et al. 1991. Effects of subchronic d–fenfluramine on splenic immune functions in young and old male and female Fischer 344 rats. Inter. J. Immunopharm. 13:1203–1212.
Clancy, J., Jr. and S. A. Lorens. 1996. Subchronic and chronic exposure to d–fenfluramine dose–dependently enhances splenic immune functions in young and old male Fischer–344 rats. Behav. Brain Res. 73:355–358.
Matthews, H.L., et al. 1996b. Effect of d–fenfluramine on the local immune response to the opportunistic microbial pathogen *Candida albicans*. Behav. Brain Res. 73:369–374.
The Merck Index, Eleventh Edition, entry 3920, p. 624.
Wurtman, USP 4,649,161, Abstract.

*Primary Examiner*—Russell Travers
*Attorney, Agent, or Firm*—The Firm of Gordon W. Hueschen

[57] ABSTRACT

The invention relates to the treatment of an immunocompromised human, e.g., an AIDS or HIV positive patient, for the enhancement of lymphocyte activity against opportunistic microbial pathogens or the treatment of any human for the enhancement of lymphocyte activity against tumors using a lymphocyte-activity-enhancing amount of dextrofenfluramine or a pharmaceutically-acceptable acid addition salt thereof.

11 Claims, No Drawings

METHOD FOR THE ENHANCEMENT OF LYMPHOCYTE ACTIVITY AGAINST OPPORTUNISTIC MICROBIAL PATHOGENS

FIELD OF THE INVENTION

The field of the invention is the treatment of humans for the enhancement of lymphocyte activity against opportunistic microbial pathogens or against tumors and, in the present case, this is effected by the administration to a living human being in need thereof of a lymphocyte-activity-enhancing amount of dextrofenfluramine or a pharmaceutically-acceptable acid addition salt thereof. The treatment of tumors may be effected in any human having the same whereas the treatment for the enhancement of lymphocyte activity against opportunistic microbial pathogens is effected in an immunocompromised human, especially a human immunocompromised by AIDS or HIV positive infection.

BACKGROUND OF THE INVENTION AND PRIOR ART

Dextrofenfluramine and its pharmaceutically-acceptable acid addition salts thereof are by now well known in the art. It is entry 3920 on page 624 of The Merck Index, Eleventh Edition, and the subject matter of French Patent M1658, U.S. Pat. Nos. 3,198,833, and 3,198,834 by Beregi et al. U.S. Pat. No. 4,309,445 by Wurtman and Wurtman discloses that dextrofenfluramine may be administered to patients having a syndrome of abnormal need for carbohydrate in order to reduce this need without inhibiting the consumption of proteins in their diet at a dosage of 10 to 60 mg per day.

U.S. Pat. No. 4,649,161 of Wurtman discloses a method for the treatment of depression using dextrofenfluramine at a dosage of 2.5. to 120 per day.

Hitzig U.S. Pat. No. 5,502,080 discloses the combined use of dopamine and serotonin agonists in the treatment of allergic disorders and treats this disorder of the immune system by administering a combination of 10 to 90 mg of fenfluramine and 15 to 500 mg of phentermine to the patient per day in single or divided doses, preferably 10 to 90 mg of fenfluramine and 15 to 160 mg of phentermine per day in single or divided doses. This patent discloses the use of fenfluramine for the treatment of immunodeficiency states such as AIDS and HIV– related diseases, and it states that patients with AIDS experience significant improvement of their T-cell counts. In addition, it states that the amount of fenfluramine administered is 10 to 120 mg/day, preferably 80 mg/day, in single or preferably divided doses of 40 mg each, and that it may be in the form of either optical isomer or a racemic mixture thereof. In the present case, it is to be noted, only dextrofenfluramine is employed.

Finally, French Patent FR 2663539, filed Jun. 22, 1990, published Dec. 27, 1991, and granted Oct. 7, 1994 discloses the employment of dextrofenfluramine or an acid addition salt thereof in a pharmaceutical composition for the production of medicinal products for the treatment of diseases due to immune deficiencies in elderly subjects at a dosage ranging from 1 mg to 15 mg per dose or per application. Such studies indicate that their results are age and sex dependent.

The method of the present invention, in contrast, is clearly not age or sex dependent in humans, and employs only about 1 to about 9 mg of dextrofenfluramine or salt thereof per day and preferably about 4.5 mg of dextrofenfluramine or salt thereof per dose, with the preferred daily dosage being between about 1 mg and 9 mg, whether to any human patient for the stimulation or enhancement of lymphocyte activity against tumors or for the treatment of immunocompromised humans, representatively those immunocompromised by AIDS or HIV positive infection, the administration of dextrofenfluramine or a pharmaceutically-acceptable acid addition salt thereof to such a patient being of a lymphocyte-activity-enhancing amount which, as will be noted, differs considerably from the type of subject previously treated, the indication being treated, and the dosage regimen involved.

In addition, previously published work by one of the inventors and others in healthy, normal animals does not in the slightest suggest that enhancement of lymphocyte activity could be effected in immunocompromised humans.

THE PRESENT INVENTION

The present invention relates to a method for the treatment of an AIDS or HIV immunocompromised human for the enhancement of lymphocyte activity against opportunistic microbial pathogens or the treatment of any human being for the enhancement of lymphocyte activity against tumors, in each case comprising the step of administering to a living human in need thereof a lymphocyte-activity-enhancing amount of dextrofenfluramine or a pharmaceutically-acceptable acid addition salt thereof, the dosage being preferably administered orally and in combination with a pharmaceutically-acceptable carrier or diluent, and the dosage preferably being between about 1 and about 9 mg per day, preferably about 4.5 mg per dose, with a daily dosage of the active ingredient dextrofenfluramine or a pharmaceutically-acceptable acid addition salt thereof ranging from about 1 to about 9 mg per day orally and up to about 6 mg per day intravenously.

Because dextrofenfluramine partially converts upon administration to its metabolite dextronorfenfluramine, one administers dextrofenfluramine in vivo but obtains both dextrofenfluramine and dextronorfenfluramine in situ, both of which are bioactive, apparently on an equimolar basis. Thus, administering 5 mg of dextrofenfluramine per os, one obtains about 5 ng/ml of dextrofenfluramine and about 3 ng of dextronorfenfluramine in tissue and in plasma.

The bioavailability of dextrofenfluramine is approximately 68% upon oral administration and the protein binding of dextrofenfluramine is about 36% whether by intravenous or oral administration. However, since the bioavailability is greater upon IV administration, a dosage of 6 mg/day by the IV route is comparable to approximately 9 mg/day by the oral route.

The method of the present invention, in contrast to previous administrations of dextrofenfluramine, employs dextrofenfluramine at an individualized dose to achieve plasma concentrations of dextrofenfluramine plus dextronorfenfluramine, its bioactive metabolite, ranging between about 1 and about 20 ng/ml. As indicated in Table 2 and Table 3, 5 ng/ml of dextrofenfluramine is more effective than 50 ng/ml so that, based upon pharmacokinetic parameters, a dose of 4.5 mg po BID should lead to steady state dextrofenfluramine and dextronorfenfluramine plasma levels in the optimal therapeutic range when administration is by the oral route, with broader ranges being between about 1 and about 9 mg/day, as previously stated.

The applicants have now discovered that the dextrofenfluramine or a pharmaceutically-acceptable acid addition salt thereof has advantageous properties applicable for the treatment of tumors and also opportunistic infections of immunodeficient patients, e.g., HIV positive or AIDS patients, due to an ability to enhance lymphocyte activity in such type of patient.

Indeed, an in-depth study in vivo of immunological parameters shows that the administration of dextrofenfluramine or a pharmaceutically-acceptable acid addition salt thereof to such subjects leads to an increase in the various immunological parameters compared with controls and thus, in general, to an unpredictable increase in immune response in such type patients.

Moreover, the doses used during these studies are doses less than those which bring about an anorexigenic action and weight loss. No effect of this type was observed during the analyses which were carried out.

OBJECTS OF THE INVENTION

It is an object of the present invention to provide a method for the treatment of an immunocompromised human, representatively a human being immunocompromised by AIDS or HIV positive infection, for the enhancement of lymphocyte activity against opportunistic microbial pathogens. It is a further object of the invention to provide a method for the treatment of any human for the enhancement of lymphocyte activity against tumors. In each case the method comprises the step of administering to a living human in need thereof a lymphocyte-activity-enhancing amount of dextrofenfluramine or a pharmaceutically-acceptable acid addition salt thereof.

A particular object of the invention is to provide such a method for the oral or intravenous treatment of an immunocompromised human, especially an AIDS or HIV positive immunocompromised human, for the enhancement of lymphocyte activity against opportunistic microbial pathogens.

Still other objects will become apparent hereinafter, and yet additional objects will be apparent to one skilled in the art to which this invention appertains.

SUMMARY OF THE INVENTION

What we believe to be our invention, then, inter alia, comprises the following, singly or in combination:

A method for the treatment of an immunocompromised human for the enhancement of lymphocyte activity against opportunistic microbial pathogens or any human against tumors comprising the step of administering to a living human in need thereof a lymphocyte-activity-enhancing amount of dextrofenfluramine or a pharmaceutically-acceptable acid addition salt thereof; such a method wherein the administration is by the oral route; such a method wherein the dextrofenfluramine is orally administered together with a pharmaceutically-acceptable carrier or diluent; such a method wherein the dextrofenfluramine is administered in amount which provides a plasma level of dextrofenfluramine and dextronorfenfluramine between about 1 and about 20 ng/ml; such a method wherein the dextrofenfluramine is administered in amount up to about 9 mg/day; such a method wherein the dosage of the dextrofenfluramine is oral and ranges from about 1 to about 9 mg per day; such a method wherein the human is immunocompromised by HIV positive; such a method wherein the human is an HIV positive human suffering from AIDS; such a method wherein the enhancement is the enhancement of the activity of human peripheral blood lymphocytes against an opportunistic microbial pathogen; such a method wherein the opportunistic microbial pathogen is a fungus; such a method wherein the opportunistic microbial pathogen is a *Candida albicans* fungus; such a method wherein the enhancement is the enhancement of the activity of human peripheral blood lymphocytes against a tumor; such a method wherein the tumor is a leukemia tumor; such a method wherein the tumor is K562 human chronic myelogenous leukemia; such a method wherein the tumor is an NK cell-sensitive tumor; such a method wherein the lymphocytes are activated by administration of a lymphocyte activator prior to administration of the dextrofenfluramine, and such a method wherein the lymphocytes are activated by administration of IL-2. (interleukin-2).

DETAILED DESCRIPTION OF THE INVENTION

The following Discussion and Examples and Pharmacology are given by way of illustration only, and are not to be construed as limiting.

I: EFFECT OF d-FENFLURAMINE (d-FEN) ON THE LYMPHOCYTE RESPONSE TO OPPORTUNISTIC MICROBIAL PATHOGENS IN IMMUNOCOMPROMISED HUMANS

Objective

The purpose of the present invention was to determine whether d-FEN would have an enhancing effect on lymphocytes obtained from immunocompromised humans. Thus, experiments were devised to determine whether d-FEN augments specific human immune parameters associated with protection from opportunistic microbial pathogens. Representative dosages of d-FEN were 5 ng/ml and 50 ng/ml of the cultured lymphocytes.

Rationale

Augmentation of specific immune parameters by d-FEN in vitro will serve as the first step in devising clinical trials for the use of d-FEN to benefit highly immunocompromised humans who are infected with the human immunodeficiency virus (HIV). The immune parameters assessed are those associated with CD8+ lymphocytes. These lymphocytes are preserved in highly immunocompromised individuals, e.g., humans with the acquired immune deficiency syndrome (AIDS). These patients have decreased levels of CD4+ lymphocytes and this reduction in the absolute numbers of CD4+ lymphocytes leads to the death of the AIDS patient. The present study focuses on d-FEN as a means by which to augment the function of CD8+ lymphocytes, which are relatively unaffected by the disease. Protection from opportunistic microbial pathogens by augmentation of such lymphocytes has the potential to significantly prolong the length of survival as well as the quality of life of highly immunocompromised humans.

General Background

The control of opportunistic microbial pathogenic infections is important for a number of clinical situations in which patients are immunosuppressed. These include not only cancer patients but also patients with cell-mediated immune defects; transplant patients treated with immunosuppressive drugs; and, most especially in patients with the AIDS. Clinical manifestations of AIDS are either due to the direct effect of the HIV or secondarily as a result of the profound immune deficiency that is a consequence of viral infection. Fungi are prominent among the opportunistic microbial pathogens that infect patients with AIDS (Dupont, 1990; Mills and Masur, 1990). The fungal diseases associated with HIV infection are the same as those found in other clinical situations characterized by depressed cellular immunity. These mycoses can be cutaneous or mucocutaneous (e.g., candidosis, dermatophytosis and pityrosporosis) or invasive (e.g., cryptococcosis, histoplasmosis and coccidioidomycosis) (Dupont, 1990). Mortality is high among immunodeficient patients infected with invasive fungi (Knobler, 1989).

The reduction in absolute numbers of CD4+ lymphocytes is the pivotal immune defect in patients with AIDS. HIV invades CD4+ cells, initiating a cascade of abnormalities in the immune system resulting in the dysfunction of normal cellular immune defenses against opportunistic microbial infections. The absence of effective cellular defenses results in the ultimate demise of AIDS patients. Opportunistic fungi account for over 50% of these infections in AIDS patients.

HIV infected individuals appear to be relatively normal for prolonged periods of time. However, as the numbers of CD4+ lymphocytes decrease in infected individuals, the incidence and severity of opportunistic infections increases. Typically, the first sign that an individual is transcending from simple HIV infection to full-blown AIDS is recurrent infection with Candida albicans. Disseminated opportunistic fungal diseases, such as histoplasmosis and coccidioidomycosis, also commonly occur in AIDS patients. Treatment of these patients with the antiviral drug, zidovudine (AZT), frequently causes neutropenia which may become severe enough to increase the patient's risk for developing systemic candidiasis.

The documented incidence of disseminated fungal disease in patients infected with HIV has dramatically increased (Panther and Sande, 1990; Sarosi and Johnson, 1990; Galgiani and Ampel, 1990). This increase not only is a consequence of better surveillance and recognition of fungal infections, but also is due to the increased incidence of HIV infected patients within geographic regions in which these fungi are endemic. AIDS patients infected with these fungi are difficult to treat, and even with aggressive chemotherapy the patient relapses with high morbidity and mortality. Polyene and available imidazoles (e.g., amphotericin B) can suppress fungal infections, but for the first time appear to have no curative effect in AIDS patients. Current treatments thus are only palliative and must include strategies for long-term administration of toxic and irritating anti-fungal agents (Davies, 1990). Thus, there is strong motive to develop other means to control opportunistic fungal infection. Treatment of patients infected with these invasive fungi require a combination of existing therapeutic regimens with new and/or alternative immunological approaches towards the management of AIDS.

Thus, d-FEN was examined in vitro for its ability to augment the activity of T lymphocytes obtained from immunocompromised individuals and thereby assess its clinical potential to enable HIV+ immunocompromised people to fight diseases caused by opportunistic microbial pathogens. Activated lymphocytes and the cytokines produced by lymphocytes exert antimicrobial effects in vivo, and provide an important host defense mechanism by which opportunistic pathogens can be limited when normal host defense mechanisms are disrupted. It is the purpose of this project to lay the groundwork by which to determine whether such cell populations can be utilized to protect individuals from opportunistic fungal infection.

Significance

Experiments were designed to determine whether d-FEN augments specific human immune parameters associated with protection from opportunistic microbial pathogens. The selected immune parameters are important for the protection of highly immunocompromised humans. Augmentation of specific human immune parameters by d-FEN in vitro would serve as the first step in devising rational clinical trials for the use of the drug to benefit highly immunocompromised humans. The immune parameters assessed are those associated with CD8+ lymphocytes. These lymphocytes are preserved in highly immunocompromised humans with AIDS who have decreased levels of CD4+ lymphocytes. The reduction in absolute numbers of CD4+ lymphocytes is the pivotal immune defect in AIDS. The present study focuses on d-FEN as a means by which to augment the function of CD8+ lymphocytes, which are relatively unaffected by the disease. Protection from opportunistic microbial pathogens by augmentation of such lymphocytes has the potential to significantly prolong the length of survival as well as the quality of life of highly immunocompromised humans. No current effective treatments exist to protect humans from the opportunistic infections associated with AIDS. The present study, therefore, provides an important step toward demonstrating that d-FEN enhances the ability of immunosuppressed patients to ward off opportunistic infections.

In the present study, we examined human T lymphocytes in three ways: 1) for their ability to kill *C. albicans* in vitro; 2) for their ability to proliferate in response to a mitogen; and, 3) their cytokine release profile (vis., their ability to release TNF-$\alpha$, IL-2 and IFN-$\gamma$).

METHODS

Subjects

The T lymphocytes analyzed were obtained from 20 HIV+ patients (9 females and 11 males, 25–48 years of age). The patients were diagnosed as being HIV+ within the past 0.5–9 years, and 15 are being treated with antiviral drugs. The subjects' study identification number (indicates the order in which bloods were drawn), CD4+ and CD8+ counts (determined March, 1996, as part of the present study), age, sex, date of diagnosis, and pharmacotherapy are provided in Table 1.

The patients fell into one of three groups (Groups A, B and C) based on their CD4+ cell counts (the number of T helper cells/$\mu$L blood): 8 of the HIV+ patients had normal (or above normal) CD4+ levels (normal range 550–1500/$\mu$L); 4 had levels between 200–499/$\mu$L; and, 7 had CD4+ counts equal to or below 200/$\mu$L. This latter group of patients by definition have AIDS (see Table 41-3 from K. J. Ryan (Ed.), *Sherris Medical Microbiology*, Third Edition, Appleton & Lange:Norwalk, Conn., 1994, p. 547). These patients, moreover, have had recurrent candidiasis and other opportunistic infections which have become increasingly difficult to manage. All of the patients' CD8+ cell (cytotoxic T lymphocytes) counts were within or above normal range (300–1000/$\mu$L). We were unable to obtain enough lymphocytes from one patient (#4) to analyze their antifungal activity.

Peripheral blood (40 ml) was drawn (Mar. 29–30, 1996) from the patients on a "first come, first serve" basis when they arrived at the Ponce Center for Diagnosis and Treatment (Dr. Hiram Valazquez, Medical Director) for their monthly checkup and who volunteered their blood for experimental analysis. In addition, blood was drawn from 4 healthy HIV– volunteers in order to study their lymphoproliferation response to Con A. The lymphocytes were isolated and processed as detailed below.

TABLE 1

Patient Profiles

| HIV+ Patient | Lymphocytes/mm³ CD4+ | Lymphocytes/mm³ CD8+ | Age | Sex | Date Diagnosed HIV+ | Treatment* |
|---|---|---|---|---|---|---|
| Non-AIDS | | | | | | |
| Group A | | | | | | |
| #1  | 1,950 | 790  | 34 | F | 04/94 | None |
| #2  | 1,300 | 1560 | 36 | M | 02/94 | None |
| #9  | 750   | 1150 | 36 | M | 09/95 | None |
| #5  | 700   | 1010 | 33 | F | 11/93 | AZT (11/93) |
| #6  | 670   | 1470 | 27 | M | 12/93 | AZT (12/93) |
|     |       |      |    |   |       | Zerit (01/96) |
| #20 | 670   | 1620 | 48 | M | 01/87 | Videx (11/94) |
| #18 | 640   | 710  | 45 | M | 02/94 | AZT (03/94) |
|     |       |      |    |   |       | Videx (11/94) |
| #12 | 600   | 1130 | 48 | F | 09/90 | AZT (08/95) |
|     |       |      |    |   |       | Zerit (02/96) |
| Group B | | | | | | |
| #11 | 410 | 750 | 33 | F | 08/94 | AZT (09/94) |
| #10 | 400 | 580 | 25 | F | 01/93 | AZT (11/94) |
| #3  | 290 | 860 | 27 | F | 08/92 | None |
| #17 | 280 | 580 | 28 | F | 05/92 | None |
| AIDS | | | | | | |
| Group C | | | | | | |
| #4  | 200 | 280  | 27 | F | 12/89   | AZT (12/93) |
| #13 | 120 | 510  | 41 | M | 05/93   | AZT (11/94) |
|     |     |      |    |   |         | Videx (10/95) |
| #7  | 80  | 1010 | 33 | M | 09/95** | AZT (09/95) |
| #16 | 50  | 840  | 36 | M | 03/92   | AZT (02/96) |
| #19 | 50  | 410  | 36 | M | 01/90   | AZT (11/93) |
| #8  | 20  | 550  | 26 | F | xx/90   | Zerit (01/96) |
| #14 | 10  | 460  | 46 | M | 09/94** | AZT (11/94) |
|     |     |      |    |   |         | Videx (10/95) |
| #15 | 0   | 550  | 30 | M | 11/94** | AZT (02/96) |

*All of the drugs being used to treat the patients are nucleoside analogs: AZT (zidovudine, Retrovir ®); Videx ® (ddI or didanosine); Zerit ® (d4T or stavudine).
**These three patients presented to the clinic with AIDS. The remaining five patients in Group C developed AIDS 2–4 years after being diagnosed HIV+. All of the AIDS patients have suffered from recurrent candidiasis; several have experienced Herpes simplex group (MCV and HSV I and II) infections; and, some have developed tuberculosis.

Experimental Protocol

The experimental protocol for this project is illustrated in Table A. Note that the cultures were exposed to two doses (5 and 50 ng/ml) of d-FEN in the mitogenesis assays, whereas only one dose (50 ng/ml) was used in the antifungal and cytokine release assays.

Immune Parameters Assessed

Isolation of Peripheral Blood Mononuclear Cells. Forty ml of venous blood were aseptically drawn into sterile 10 ml tubes containing 20 U/ml preservative free heparin, diluted with an equal volume of Hank's Balanced Salt Solution (HBSS), layered over Lymphocyte Separation Medium (LSM, Bionetics, Kensington, Md.), and centrifuged at 1,000×g for 30 min. After centrifugation, the mononuclear cell layer was recovered from the interface and washed twice in HBSS prior to further manipulation and then enumerated microscopically.

Lymphocyte Mediated Antifungal Activity Against Candida albicans: Fungal Culture. C. albicans cultures were stored at 25° C. on Sabouraud's dextrose agar (SDA) (Becton Dickinson and Co., Cockeysville, Md.). Cells used for experimentation were cultured overnight at 37° C. on SDA, collected as isolated colonies, and washed once in HBSS. Yeast cultures were enumerated microscopically. C. albicans were inoculated into RPMI 1640 medium. C. albicans hyphal forms were obtained by incubation at 37° C. with 5% $CO_2$ in RPMI 1640. Inoculum of $2 \times 10^5$ yeast cells/ml yield approximately 100% hyphal fragments when incubated for 2 h at 37° C.

Activation of Lymphocytes. Human peripheral blood lymphocytes were placed in culture medium containing $5 \times 10^{-5}$ 2-mercaptoethanol (2-ME) at a concentration of $2.0 \times 10^6$ cells/ml with d-FEN (50 ng/ml was added on the second day of culture) and 1,500 U/ml IL-2 (Hoffman-La Roche Inc., Nutley, N.J.) in Falcon, Multiwell plates (Becton Dickinson, Lincoln Park, N.J.) for 3 and 4 days. The cells were harvested following incubation at 37° C., overlaid onto LSM and centrifuged at 1,000×g for 20 min. The cells at the interface were washed twice with HBSS prior to assessment of functional activity.

Measurement of the Inhibition of C. albicans Growth. Fungal cells used for experimentation were collected from isolated, overnight colonies on SDA, and washed once in HBSS. Yeast were resuspended to $2 \times 10^5$/ml in RPMI 1640 and $5 \times 10^3$ yeast placed in individual wells of 96 well flat bottom plates (Corning Glass Works, #25861, Corning, N.Y.). These plates were incubated at 37° C. in 5% $CO_2$ for 2 h to obtain C. albicans hyphal forms. d-FEN (50 ng/ml was added the on the second day of culture) and IL-2 activated lymphocytes (at effector to target ratios ranging from 50:1 to 6:1) were transferred to C. albicans hyphae and incubated together for 3 h at 37° in 5% $CO_2$. At the end of this period lymphocytes were removed by washing with a PHD cell harvester (Cambridge Technology, Cambridge, Mass.). Subsequently, 1.0 μCi of [$^3$H]uridine/well in 50 μl HBSS was added to the hyphae. Following 1 h incubation at 37° C., 25 U lyticase (Sigma Chemical, St. Louis, Mo.) in 50 ul HBSS was added per well for 1 h at 25° C. Fungal cells then were harvested using a PHD cell harvester and DPM determined. Lyticase loosens the hyphae and permits them to be aspirated onto glass fiber filter strips. The detailed technique has been published (Beno and Mathews, 1993).

TABLE A

EXPERIMENTAL PROTOCOL

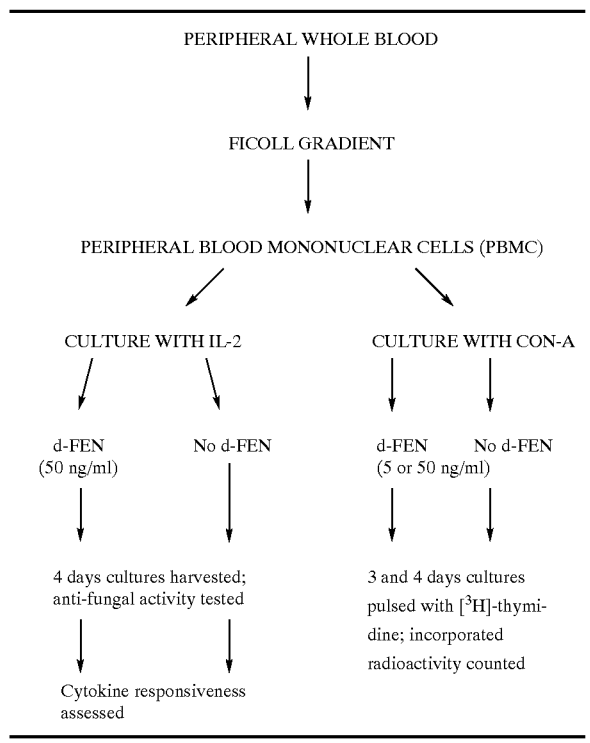

The results were expressed as % growth inhibition and calculated by the formula: % growth inhibition of C. albicans={[DPM C. albicans alone—(DPM of sample—DPM of lymphocytes alone)]/DPM C. albicans alone}×100. All cultures were prepared at least in triplicate and the mean % inhibition of those values determined. Inhibitory units (IU) were calculated as the number of cells per $10^7$ effectors required to achieve 20% growth inhibition of the fungal target. Growth inhibition was calculated using a computer program written by David Coggins (FCRC, Frederick, Md.).

Cytokine Profiles. Peripheral mononuclear cells were isolated by the Ficoll-Hypaque method and washed twice with RPMI-1640 medium. Cell suspensions were made at 1×10$^6$/ml and the cells activated with interleukin-2 (IL-2) for 18 h or 4 days at 37° C. under 5% $CO^2$+95% air. Monensin (1 nM) then was added to the culture to block secretion of cytokines, and the cultures allowed to continue for another 3 h. The cells were washed twice with PBS+1% fetal calf serum (FCS) with 0.1% saponin+0.1% sodium azide, then washed once with PBS-1% FCS and stained with anti-cytokine MAb-FL conjugate for 30 min. Following two washes, the cells were analyzed by flow cytometry for production of IL-2, IFN-γ and TNF-α. The MAbs-FL conjugates were obtained from Pharmingen (San Diego, Calif.). Potential effects of on cytokine production were evaluated (a) as increases in the percentage of a T cell subset which produce the respective cytokine; and, (b) as increases in the amount of cytokine produced by each subset. The latter were analyzed as a shift of the cytokine histograms.

Cell Proliferation Analysis. Lymphoid cell suspensions were cultured in microtiter plates (Corning Glass Works, Corning, N.Y.) in the presence of 3.0 μg/ml Con-A (Pharmacia, Uppsala, Sweden) for 3 and 4 days at 37° C. d-FEN (5 and 50 ng/ml) was added the second day of culture. The cells were cultured at 2×10$^5$/well in RPMI 1640 with 1% fetal bovine serum. The cells then were pulsed for 6.0 h with 1.0 μCi of [$^3$H]-thymidine (DuPont-New England Nuclear Research, Boston, Mass.), harvested, and [$^3$H]-thymidine incorporation determined with a liquid scintillation counter. The data are reported as a percent increase in the stimulation in dextrofenfluramine values.

Data Analysis

The data were analyzed by a one- or two-way analysis of variance (ANOVA) with repeated measures where appropriate (SIGMASTAT version 1; Jandel, San Rafael, Calif.). Significant main effects were subjected to post hoc analysis using the Student-Newman Keuls All Pairwise Multiple Comparisons test or the Mann-Whitney U test.

RESULTS

Antifungal Activity

The antifungal data in Table 2 are expressed in antifungal units, a measure of fungal growth inhibition as detailed in Beno and Mathews (1992) and Beno et al. (1995). As can be seen (Table 2), 7 of the 8 "normal" (Group A) patients showed increased antifungal activity when their lymphocytes were cultured with d-FEN and compared with their lymphocytes cultured without d-FEN (mean increase of 23%). One patient (#9) showed a decrease in antifungal activity (−172 units) in the presence of d-FEN. The 4 patients in Group B showed a mixed response. However, all 7 of the AIDS patients (Group C) evidenced increased (+100%) antifungal activity in the presence of d-FEN. A one-way ANOVA (followed by the Student-Newman-Keuls test) showed that the antifungal activity of Group C was significantly greater in the presence of d-FEN ($F=12.6$; $df=2,18$; $p<0.001$) than the other two groups. The increase in killing ability (column Δ) also was significant ($F=6.7$; $df=2$, $18$; $p=0.008$). These data provide direct evidence that d-FEN (50 ng/ml) enhances the in vitro antifungal activity of lymphocytes obtained from AIDS patients.

Concanavalin A (Con A) Induced T Cell Lyphoproliferation

Table 3 contains the results from the Con A mitogenesis study. A two way analysis of variance (ANOVA) revealed significant group ($F=3.9$; $df=2,45$; $p=0.028$) and interaction ($F=9.9$; $df=2,45$; $p<0.001$) effects. The dose effect did not reach significance ($F=2.2$; $df=1,45$; $p=0.15$). The post hoc analysis (Mann Whitney U Test) showed that the human controls (n=4) and AIDS patients (Group C; n=7) showed greater mitogenesis in the presence of 5 ng/ml d-FEN than the non-AIDS HIV+ patients (Groups A and B combined; n=12). The human controls and AIDS patients did not differ. In contrast, the non-AIDS HIV+ patients (Groups A+B) showed greater mitogenesis than the AIDS group (Group C) when their cultured lymphocytes were exposed to 50 ng/ml d-FEN. Note that AIDS patient #15 did not show any proliferation since this subject had no detectable CD4+ cells to stimulate (an excellent internal assay control). These results indicate that lymphocytes obtained from human control and AIDS subjects respond better in vitro to a low (5 ng/ml) than to a high (50 ng/ml) dose of d-FEN; cells obtained from the non-AIDS HIV+ subjects showed the opposite effect. Thus, d-FEN not only enhances the antifungal activity of CD8+ lymphocytes obtained from AIDS patients but also increases mitogenesis of CD4+ cells obtained from the same patients. Clearly, this combination of effects would be most beneficial to AIDS patients. In addition, these observations suggest that the efficacy of nucleoside analog and/or protease inhibitor therapy (see The Medical Letter report (Apr. 12, 1996)) would likely be enhanced by supplemental low dose d-FEN treatment.

Percent Cytokine Immunopositive T Cells and Cytokine Levels

INF-γ, IL-2 and TNF-α are soluble proteins produced by T lymphocytes that act on other T lymphocytes, on NK, cells and on macrophages to augment immune responses and lympho-responsiveness. These cytokines influence the growth, differentiation and activity of the indicated cell populations. Specifically, INF-γ is a powerful activator of such cells. It is best known as the activator of macrophages to increase their antimicrobial activity. IL-2 is a well characterized T lymphocyte growth factor essential to the effective clonal expansion and development of the T lymphocyte mediated immune response. TNF-α is a powerful modulator of immune responses including the induction of adhesion molecules, other cytokines and the activation of not only the above mentioned cells but also polymorphonuclear leukocytes. TNF-α is essential in the resistance to microbial infections (e.g., mycobacteria).

CD4+ and CD8+ T lymphocytes obtained from AIDS and non-AIDS HIV+ humans were analyzed in vitro in two ways: 1) the % of cultured T cells cytokine immunopositive; and, 2) the titer or amount of cytokine produced. Any d-FEN induced increase in % immunopositive T cells or cytokine titer suggests that d-FEN enhances immune responsiveness. Increased INF-γ would increase the capacity and number of macrophages to kill microorganisms. Increased IL-2 would expand activated T lymphocyte populations to a greater extent. Increased TNF-α would lead to more powerful antimicrobial effector mechanisms.

A. Interleukin-2 (IL-2)

CD4+ (CD8−) T Cells. The two-way ANOVA (repeated measures) of the percent IL-2 immunopositive cells demonstrated a significant group effect (F=25.7; df=1,18; p<0.001). As seen in Table 4, the AIDS patients evidenced a 75% decrease in the number of IL-2+ CD4+ T cells. The ANOVA of the IL-2 titer in the CD4+ lymphocytes showed a significant group effect (F=12.2; p=0.003). The drug (F=3.6; p=0.07) and interaction (F=3.7; p=0.07) effects were not statistically significant. However, the post hoc analysis (Student-Newman-Keuls test) showed that d-FEN significantly enhanced (55%) IL-2 levels in the AIDS but not in the non-AIDS patients' CD4+ T cells (Table 4).

CD8+ T Cells. The ANOVAs revealed effects on CD8+ T cells which mirrored those found in the CD4+ cells. Thus, the percent IL-2+ T cells from the AIDS patients were significantly (F=12.9; df=1,18; p=0.002) lower (50%) than the IL-2+ cells from the non-AIDS patients. The post hoc analysis following the ANOVA (group F=4.3, p=0.05; drug F=3.6, p=0.07) demonstrated that d-FEN enhanced (40%) the titer of IL-2 in the CD8+ cells taken from the AIDS but not from the non-AIDS patients (Table 4).

B. Interferon-gamma (INF-γ)

CD4+ (CD8−) T Cells. As seen in Table 5, d-FEN significantly (F=9.3; df=1,18; p=0.007) increased (33–38%) the percent of immunopositive INF-γ T cells taken from all patients. INF-γ levels were significantly (F=8.2; df=1,18; p=0.007) lower (29–33%) in the AIDS than in the non-AIDS derived CD4+ lymphocytes, but d-FEN did not have any significant effect.

CD8+ T Cells. No significant differences were observed.

C. Tumor Necrosis Factor-alpha (TNF-α)

CD4+ (CD8−) T Cells. The AIDS patients demonstrated significantly (F=70.2; df=1,18; p<0.001) reduced numbers of TNF-α+ CD4+ T cells (55–61%) which d-FEN failed to affect. A significant group effect (F=8.5; df=1,18; p<0.009) also was observed on TNF-α titer which was reduced by 50–62% in the AIDS derived T cells. The post hoc analysis showed that the 50 ng/ml dose of d-FEN reduced (23%) the level of TNF-α in non-AIDS but not in the AIDS CD4+ T cells (Table 6). This was the only inhibitory effect of d-FEN observed in the present study. It is likely that this effect is due to the high dose of d-FEN employed. No other effects of d-FEN on CD4+ T cells were found.

CD8+ T Cells. The ANOVA revealed a significant group effect (F=8.5; df=1,18; p=0.009) on percent CD8+ T cells positive for TNF-α. The post hoc analysis showed that this main effect was due to the lower (28%) number of TNF-α+ cells obtained from the AIDS patients, and to the d-FEN induced increase (24%) in their number (Table 6). No significant effects on TNF-α titer were observed.

DISCUSSION

It is clear from these data that d-FEN augments a variety of antimicrobial immunological parameters. The most dramatic were observed on the lymphocytes obtained from AIDS patients. All of the AIDS patients' lymphocytes increased their antimicrobial activity when treated with d-FEN In vitro. The results also show that with extended in vitro culture d-FEN can increase the antimicrobial activity of human lymphocytes for *C. albicans,* and clearly demonstrate the potential for d-FEN as a means by which to augment antimicrobial immunity in highly immunocompromised individuals. Likewise, d-FEN was shown to augment mitogen induced lymphoproliferation most effectively in T cells obtained from AIDS patients. Further, 5 ng/ml d-FEN was capable of inducing greater lymphoproliferation in AIDS derived lymphocytes than 50 ng/ml. The direct antimicrobial activity of CD8+ lymphocytes, coupled with the enhanced capacity of CD4+ lymphocytes to proliferate when treated with d-FEN, indicates that d-FEN has the potential to markedly augment immune function in highly immunocompromised people.

The data reported above demonstrate the ability of d-FEN to enhance the capacity of CD4+ and CD8+ lymphocytes to produce cytokines. Moreover, d-FEN does not adversely affect the capacity of lymphocytes from AIDS patients to produce cytokines. Finally, these cytokines can serve to augment antifungal activity.

CONCLUSIONS 1. d-FEN augments the capacity of CD8+ lymphocytes to kill the opportunistic microbial pathogen, *Candida albicans.*
2. d-FEN enhances the capacity of CD4+ lymphocytes to proliferate in response to a broadly active mitogenic stimulus, Con A.
3. d-FEN increases the amount (titer) of IL-2 produced by CD4+ and CD8+ lymphocytes from AIDS patients.
4. d-FEN increases the number of CD4+ and CD8+ lymphocytes obtained from both non-AIDS and AIDS patients that produce IFN-γ.
5. d-FEN increases the number of AIDS patients' CD8+ lymphocytes that produce TNF-α, but decreases the amount of TNF-α produced by CD4+ lymphocytes obtained from non-AIDS HIV+ patients.
6. d-FEN increases the responsiveness of lymphocytes to produce two important cytokines, IL-2 and IFN-γ. These cytokines are the hallmark cytokines produced by the $T_H1$ lymphocyte subpopulation. This subpopulation of T lymphocytes is considered essential for the effective elimination of microbial pathogens associated with AIDS.
7. The preclinical data we have obtained using mice and rats, as well as our in vitro human data, evidences that low subanorectic doses of d-FEN are effective in enhancing immune function, especially in severely immunocompromised AIDS patients.

TABLE 2

Effect of Dexfenfluramine (50 ng/ml) on the Ability of Human Lymphocytes to Kill *C. Albicans* in vitro.

| HIV+ Patient Group & No. | | CD4+ | CD8+ | Antifungal Units No d-FEN | Antifungal Units d-FEN | Δ |
|---|---|---|---|---|---|---|
| A | 1 | 1950 | 790 | 25 | 62 | 37 |
|   | 2 | 1300 | 1560 | 69 | 84 | 15 |
|   | 9 | 750 | 1150 | 254 | 82 | −172 |
|   | 5 | 700 | 1010 | 76 | 144 | 68 |
|   | 6 | 670 | 1470 | 10 | 31 | 21 |
|   | 20 | 670 | 1620 | 11 | 60 | 49 |
|   | 18 | 640 | 710 | 56 | 60 | 4 |
|   | 12 | 600 | 1130 | 117 | 236 | 119 |
| Mean + SEM | | | | 77 ± 28 | 95 ± 23 | 18 ± 30 (+23%) |
| B | 11 | 410 | 750 | 104 | 16 | −88 |
|   | 10 | 400 | 580 | 66 | 164 | 98 |
|   | 3 | 290 | 860 | 114 | 120 | 6 |
|   | 17 | 280 | 580 | 148 | 75 | −73 |
| Mean + SEM | | | | 108 ± 17 | 94 ± 32 | −14 ± 43 (−13%) |
| C | 13 | 120 | 510 | 19 | 130 | 111 |
|   | 7 | 80 | 1010 | 59 | 321 | 262 |
|   | 16 | 50 | 840 | 119 | 164 | 46 |
|   | 19 | 50 | 410 | 217 | 355 | 138 |
|   | 8 | 20 | 550 | 189 | 307 | 118 |
|   | 14 | 10 | 460 | 168 | 314 | 146 |
|   | 15 | 0 | 550 | 225 | 394 | 169 |
| Mean + SEM | | | | 142 ± 30 | 284 ± 37* | 141 ± 24* (+100%) |

*Significantly (p < 0.05) greater than the other two groups.

TABLE 3

Dose-dependent Effects of Dexfenfluramine (d-FEN) on CD4+ Lymphoproliferation

| Group/Subject Number | CD4+ Lymphocytes/ mm³ | Increase in Index of Stimulation [%]^A 5 ng/ml d-FEN | Increase in Index of Stimulation [%]^A 50 ng/ml d-FEN |
|---|---|---|---|
| NORMAL CONTROLS (HIV−) | | | |
| #1 | NT^B | 82 | 12 |
| #2 | NT | 34 | 21 |
| #3 | NT | 93 | 95 |
| #4 | NT | 100 | 58 |
| Mean ± SEM | | 77 ± 13* | 47 ± 13 |
| HIV+ PATIENTS | | | |
| Group A | | | |
| #1 | 1,950 | 20 | 47 |
| #2 | 1,300 | 34 | 29 |
| #9 | 750 | 30 | 96 |
| #5 | 700 | 30 | 0 |
| #6 | 670 | 0 | 34 |
| #20 | 670 | 33 | 80 |
| #18 | 640 | 0 | 77 |
| #12 | 600 | 31 | 68 |
| Group B | | | |
| #11 | 410 | 11 | 23 |
| #10 | 400 | 6 | 58 |
| #3 | 290 | 10 | 22 |
| #17 | 280 | 0 | 60 |
| Groups A + B^C | | | |
| Mean ± SEM | | 17 ± 8 | 50 ± 8** |
| Group C | | | |
| #4 | 200 | 60 | 0 |
| #13 | 120 | 83 | 0 |
| #7 | 80 | 32 | 0 |
| #16 | 50 | 10 | 18 |
| #19 | 50 | 38 | 76 |
| #8 | 20 | 62 | 0 |
| #14 | 10 | 87 | 0 |
| #15 | (0) | (0) | (0) |
| Mean ± SEM^D | | 50 ± 10* | 13 ± 10 |

^A The stimulatory effect of d-FEN is expressed as a percent increase in the stimulation index of PBMCs cultured with the two doses of d-FEN versus that cultured without d-FEN. The data represent the greatest stimulation that occurred after the lymphocytes had been in culture for 3 or 4 days. The mitogenic activity of the PBMC (CD4+ lymphocytes) index of stimulation was calculated as follows:

$$\frac{\text{CPM Con A Stimulated d-FEN Culture}}{\text{CPM Unstimulated Culture}} \times 100 = \% \text{ Change}$$

^B NT: Not tested since these subjects were not HIV+.
^C Groups A and B are non-AIDS HIV+ subjects. As no differences were discerned between these two groups, they were combined for the statistical analysis.
^D Subject #15 was not included in the statistical analysis since this subject did not have any CD4+ lymphocytes that could proliferate in response to Con A stimulation.
*Significantly (p < 0.05) greater than Groups A + B. Two way ANOVA followed by a Mann-Whitney U Test.
**Significantly (p < 0.05) greater than Group C. Two way ANOVA followed by a Mann-Whitney U Test.

TABLE 4

Effect of d-FEN (50 ng/ml) In Vitro on Percent
IL-2 Positive Cells and IL-2 Titer in CD4+ and CD8+ T Lymphocytes Obtained from HIV+ Humans with AIDS (n = 8) and without AIDS (non-AIDS; n = 12).

| HIV+ Patient | % Positive Cells | | Titer | |
|---|---|---|---|---|
| Group | VEH | d-FEN | VEH | d-FEN |
| CD4+ (CD8−) T Cells | | | | |
| Non-AIDS | 32 ± 3* | 32 ± 3* | 308 ± 27* | 308 ± 27* |
| AIDS | 8 ± 4 | 9 ± 4 | 137 ± 33 | 213 ± 33** |
| | | | | (+55%) |
| CD8+ T Cells | | | | |
| Non-AIDS | 37 ± 3* | 36 ± 3* | 205 ± 28* | 220 ± 28* |
| AIDS | 19 ± 4 | 18 ± 4 | 105 ± 34 | 147 ± 34** |
| | | | | (+40%) |

Values expressed as Mean ± SEM. Numbers in parentheses represent the percent increase over corresponding vehicle control (VEH) treatment in vitro.
% Positive Cells = percent of cultured T cells which were immunopositive for IL-2.
Titer = geometric mean channel fluorescence.
*Significantly ($p < 0.05$) greater than AIDS patients (two-way ANOVA followed by Student-Newman-Keuls test).
**Significantly ($p < 0.05$) greater than VEH.

TABLE 5

Effect of d-FEN (50 ng/ml) In Vitro on Percent
INF-γ Positive Cells and INF-γ Titer in CD4+ and CD8+ T Lymphocytes Obtained from HIV+ Humans with AIDS (n = 8) and without AIDS (non-AIDS; n = 12).

| HIV+ Patient | % Positive Cells | | Titer | |
|---|---|---|---|---|
| Group | VEH | d-FEN | VEH | d-FEN |
| CD4+ (CD8−) T Cells | | | | |
| Non-AIDS | 12 ± 2 | 16 ± 2** | 413 ± 37* | 473 ± 37* |
| | | | | (+33%) |
| AIDS | 13 ± 2 | 18 ± 2** | 277 ± 45 | 336 ± 45 |
| | | | | (+38%) |
| CD8+ T Cells | | | | |
| Non-AIDS | 41 ± 4 | 47 ± 4 | 845 ± 71 | 964 ± 71 |
| AIDS | 39 ± 5 | 40 ± 5 | 715 ± 86 | 764 ± 86 |

Values expressed as Mean ± SEM. Numbers in parentheses represent the percent increase over corresponding vehicle control (VEH) treatment in vitro.
% Positive Cells = percent of cultured T cells which were immunopositive for INF-γ.
Titer = geometric mean channel fluorescence.
*Significantly ($p < 0.05$) greater than AIDS patients (two-way ANOVA followed by Student-Newman-Keuls test).
**Significantly ($p < 0.05$) greater than VEH.

TABLE 6

Effect of d-FEN (50 ng/ml) In Vitro on Percent
TNF-α Positive Cells and TNF-α Titer in CD4+ and CD8+ T Lymphocytes Obtained from HIV+ Humans with AIDS (n = 8) and without AIDS (non-AIDS; n = 12).

| HIV+ Patient | % Positive Cells | | Titer | |
|---|---|---|---|---|
| Group | VEH | d-FEN | VEH | d-FEN |
| CD4+ (CD8−) T Cells | | | | |
| Non-AIDS | 72 ± 3* | 69 ± 3* | 406 ± 32* | 310 ± 40*ᵛ |
| | | | | (−23%) |
| AIDS | 28 ± 4 | 31 ± 4 | 154 ± 40 | 156 ± 40 |
| CD8+ T Cells | | | | |
| Non-AIDS | 69 ± 3* | 69 ± 3 | 347 ± 47 | 392 ± 47 |
| AIDS | 50 ± 4 | 62 ± 4** | 270 ± 57 | 329 ± 57 |
| | | (±24%) | | |

Values expressed as Mean ± SEM. Numbers in parentheses represent the percent increase over corresponding vehicle control (VEH) treatment in vitro.
% Positive Cells = percent of cultured T cells which were immunopositive for TNF-α.
Titer = geometric mean channel fluorescence.
*Significantly ($p < 0.05$) greater than AIDS patients (two-way ANOVA followed by Student-Newman-Keuls test).
ᵛSignificantly ($p < 0.05$) less than VEH.
**Significantly ($p < 0.05$) greater than VEH.

II. EFFECT OF d-FENFLURAMINE (d-FEN) ON THE HUMAN IMMUNE RESPONSE TO TUMORS

OBJECTIVE

The purpose of the present experiments was to determine whether d-FEN can enhance the ability of the human immune system to kill a human tumor cell line, vis. K562 human chronic myelogenous leukemia cells. Toward this end d-FEN and vehicle (VEH) treated young male severe combined immunodeficient (SCID) beige mice, reconstituted 4 days previously with human peripheral blood mononuclear cells (PBMC) obtained from two human volunteers, were injected with K562 cells and tumor size and number measured 13–18 days later.

METHODS

A. Severe Combined Immunodeficient (SCID) Mouse Study
Animals

SCID mice (n=36) were obtained from Harlan Sprague-Dawley Inc. (Indianapolis, Ind.). This inbred strain of mice are devoid of T, B, and natural killer (NK) cells. The animals were housed 3/cage in an AAALAC approved facility with a 12 h light-dark cycle (lights on at 07:00 h). The temperature and humidity of the facility were maintained between 72–75° F. and 52–55% respectively. Food (Purina mouse chow) and water were available ad libitum.

Drug Plasma Levels. At the time of sacrifice, serum was collected by cardiac puncture, the plasma separated and frozen, then air expressed to Dr. Bruce Campbell (Servier UK) for analysis of d-FEN and d-norFEN levels.

Protocol. The animals were divided into groups of 6 and subjected to the following treatment for each of the 2 human donors tested:

| | | | | |
|---|---|---|---|---|
| 1. | Den + | Human PBMC | + K562 | 2 × 6 mice |
| 2. | None | Human PBMC | + K562 | 2 × 6 mice |
| 3. | None | None | K562 | 2 × 6 mice |

The mice treated with d-FEN (10 mg/kg/day, p.o.) received the drug daily in their drinking water beginning 10 days prior to inoculation with human PBMC. On the day of PBMC injection ($3 \times 10^7$ human PBMC/mouse, i.p.) the dose of d-FEN was reduced to 6 mg/ml/day. The average daily water intakes and body weights of the mice were 6 ml and 20 g, respectively. Therefore, a dose of 6 mg/kg equaled 2 mg of d-FEN per 100 ml of water. Four days after reconstitution with human PBMC, $1 \times 10^7$ K562 human tumor cells/mouse were injected i.p. The animals were sacrificed between 11:00 and 13:00 h 13–18 days after K562 cell injection (17–22 and 27–32 days, respectively, after transfection with human PBMC and the start of d-FEN treatment). The animals were thoroughly necropsied and tumor sites counted, excised, weighed and fixed for histological analysis.

B. Human In Vitro Study

Prior to conducting the above experiment, we examined the dose dependent effects of d-FEN on the ability of human PBMC obtained from five healthy volunteers (male Caucasians in their mid-twenties) to kill human K562 tumor cells in vitro. The potential cytotoxic enhancing effects of d-FEN and d-norFEN were compared using PBMC from two of the five human donors.

Isolation of Peripheral Blood Mononuclear Leukocytes

For assessment of immunological parameters of human PBMC, venous blood as aseptically drawn into sterile 10 ml tubes containing 20 U/ml preservative free heparin, diluted with an equal volume of Hank's Balanced Salt Solution (HBSS), layered over Lymphocyte Separation Medium (LSM, Bionetics, Kensington, Md.) and centrifuged at 1,000 ×g for 30 min. After centrifugation, the mononuclear cell layer was recovered from the interface and washed twice in HBSS and enumerated.

For reconstitution of SCID mice with human PBMC, 500 ml of venous blood was drawn into sterile plastic pouches containing preservative free heparin. Blood was drawn by Apheresis Lab nurses at LUMC (Loyola University Medical Center) and was diluted with an equal volume of HBSS. The diluted blood (20 ml) was layered over 10 ml of Histopaque 1077 (Sigma Chemical Company, St. Louis, Mo.) and centrifuged at 1000×g for 30 min. After centrifugation, the mononuclear cell layer was recovered from the interface and washed twice in HBSS. After microscopic enumeration, the PBMC were resuspended in HBSS at a concentration of $1 \times 10^8$ cells/ml, and 0.3 ml ($3 \times 10^7$ cells) of the cell suspension was injected (i.p.) into each SCID mouse.

Tumor Cell Line

The K562 cell line originated from a chronic myelogenous leukemia patient and was obtained from Dr. T. Ellis (Director, Cellular Immunology Laboratory, LUMC). The K562 cells used for assessment of cytotoxic activity were maintained in long term cultures using Corning 25 cm² tissue culture flasks (Corning Glass Works, Corning, N.Y.) containing RPMI 1640 (Gibco Laboratories, Grand Island, N.Y.) supplemented with low LPS 10% fetal bovine serum (FBS; Gibco), 100 units/ml penicillin, 100 µg/ml streptomycin (Whittaker M. A. Bioproducts, Walkersville, Md.), 0.1 mM non-essential amino acids, and 2 mM L-glutamine (Gibco). This medium was used throughout, except where noted, and is referred to as "culture medium". The K562 cells were grown in suspension and were passaged three times per week by transfer of $10^6$ K562 cells into a flask containing 10 ml of fresh culture medium. The K562 cells injected into the SCID mice were supplemented with fresh medium at a 1:3 dilution the day before administration. They were washed once in medium, pelleted by centrifugation at 500 ×g for 10 min., then resuspended at a concentration of $5 \times 10^7$. Subsequently, 0.2 ml ($1 \times 10^7$ cells) of the cell suspension was injected (i.p.) into each SCID mouse. The K562 cells were administered to the animals four days after the injection of PBMC.

Natural Killer Cell Cytotoxicity Assay

The K562 tumor cell lines maintained in vitro were washed once in culture medium, pelleted by centrifugation at 500×g for 10 min and resuspended in approximately 0.1 ml of culture medium. Subsequently, 100 µCi of [$^{51}$Cr] (New England Nuclear, Boston, Mass.) was added to $1 \times 10^5$ cells in a final volume of 0.2 ml. The cells were incubated at 37° C. with 5% $CO_2$ for 1 h with agitation every 10 min, then washed 3 times in HBSS, resuspended to $5 \times 10^4$ cells/ml in culture medium and 0.1 ml ($5 \times 10^3$) aliquoted to each well of a 96 well round bottom assay plate (Corning Glass Works, Corning, N.Y.). Radiolabelled K562 was cultured for 4 h with lymphocytes at effector to target ratios ranging from 50:1 to 6:1. Following 4 h of culture the media was removed using a Skatron harvesting press (Skatron Inc., Sterling, Va.) and associated radioactivity determined. Maximum release was obtained by adding 0.05% Nonidet P-40 (Sigma Chemical Co., St. Louis, Mo.).

The results have been expressed as % cytotoxicity and calculated by the formula: % cytotoxicity=[(experimental DPM−minimum DPM)/(maximum DPM−minimum DPM)]×100.

All experimental means were calculated from triplicate values. Lytic units (LU) were calculated using a computer program written by David Coggins, FCRC, Frederick, Md.

RESULTS

A. SCID Mouse Study

Animals. The body weights and water intakes of the d-FEN treated SCID mice did not differ from those of the control animals (Table I).

Plasma d-FEN and d-norFEN Levels. Neither d-FEN nor d-norFEN was detected. This absence of drug and metabolite detectability may not only be due to the low oral dose of d-FEN employed but to the time of sacrifice. Mice like rats are prandial drinkers during the dark period of the light-dark cycle. The animals were sacrificed between 11:00 and 13:00 h, 4–6 h after the end of the dark period. Since the t1/2s of d-FEN and d-norFEN in the mouse are 4 and 6 h, respectively, by the time of sacrifice the plasma concentrations had likely fallen below the levels of assay detectability.

Tumor Incidence and Metastasis

The mice treated with d-FEN evidenced a significantly (p=0.05) reduced incidence of histopathologically confirmed lymphomas (Table I). Although the number of d-FEN treated mice (8%) showing tumor metastasis was considerably less than that in the other two groups (38%), this observation did not reach significance (p=0.6). One of the d-FEN treated mice had the largest tumor (0.833 g) and evidenced metastasis.

B. Human In Vitro Study

Prior to conducting the above experiment, we examined the dose dependent effects of d-FEN on the ability of human PBMC obtained from five healthy volunteers (male Caucasians in their mid-twenties) to kill human K562 tumor cells in vitro. As seen in Table II, low doses of d-FEN enhanced whereas higher doses reduced cytotoxicity (F=78; df=6,23; p<0.001). In addition, d-FEN and d-norFEN produced virtually identical effects (Table III).

DISCUSSION

It is clear from these data that d-FEN augments NK activity in vitro and anti-tumor activity in vivo. The immunomodulatory effect of any drug must first be documented in experimental systems prior to an analysis of its effects in humans. In experimental animal models d-FEN has been shown to augment T and B lymphocyte functions, to increase cell-mediated cytotoxicity for natural killer cell (NK) tumor targets and to enhance cell-mediated activities for opportunistic microbial pathogens (Clancy and Lorens, 1996; Mathews et al., 1996). D-FEN appears to effect the immune system as a 5-HT releaser and reuptake inhibitor resulting in an augmentation of NK activity and an increase in lymphocyte proliferation. The drug also appears to increase the influx of lymphocytes into lymph nodes and serves to augment the overall anti-fungal activity of infectious site associated lymphocytes (Mathews et al., 1996). In vivo, D-FEN appears to bias the protective immune response toward the T cell compartment of the immune system. In vitro, stimulatory effects by 5-HT on human percoll-fractionated peripheral blood lymphocytes mediated NK activity have been reported. Such stimulation was 5-HT dose dependent, lasted 16 h, and was due to a prostaglandin independent, non-interferon, non IL-2 like factor released from plastic nonadherent monocytes. However, a complete analysis of these d-FEN effects has not been performed in humans.

In this investigation a single important issue is addressed with regard to the effect of d-FEN treatment on the immune system. This study demonstrates d-FEN to modulate immune parameters in SCID mice (which are devoid of T, B, and NK cells) reconstituted with human PBMC. The results clearly show that in this experimental model human immune responsiveness to human tumors can be augmented by d-FEN.

These results are in agreement with our chronic d-FEN study (Clancy and Lorens, 1996) and other preclinical data. Overall, the data indicate that d-FEN enhances the ability of the human immune system to fight natural killer cell (NK) sensitive tumor cells, such as K562, which invade humans.

CONCLUSIONS 1. d-FEN, as well as d-norFEN, augments the capacity of human NK cells to kill the human tumor cell line, K562.
2. d-FEN enhances the capacity of immunodeficient mice, reconstituted with human PBMC, to resist the development of human tumors.
3. d-FEN and d-norFEN appear to exert their anti-tumor effect by augmenting the anti-tumor activity of human immune cells.
4. Our published preclinical data using mice and rats, as well as our human data, indicate that low subanorectic doses of d-FEN are effective in enhancing immune function against tumor cells both in vitro and in vivo.

TABLE I

EFFECT OF d-FEN* ON THE INCIDENCE AND METASTASIS OF HUMAN LYMPHOMAS (K652) IN SCID MICE TRANSFECTED WITH HUMAN PBMC

| Treatment | K562 | K562 + PBMC | K562 + PBMC + d-FEN |
|---|---|---|---|
| Body Weight (g) | 19.5 ± 1.5 | 17.6 ± 2.6 | 17.5 ± 2.1 |
| Number of Mice Having Tumors | 9/12 (75%) 18/24 (75%) | 9/12 (75%) | 5/12 (42%)** |
| Number of Mice Showing Multiple Tumor Sites | 4/12 (33%) 9/24 (38%) | 5/12 (42%) | 1/12 (8%) |

*d-FEN (10 mg/kg/day) was administered in the animals' drinking water starting 10 days before adoptive transfer with human PBMC; the dose then was reduced to 6 mg/kg/day. The animals received d-FEN daily until sacrificed.
**Significantly (p = 0.05) less than the other two groups combined (Fisher Exact Probability Test).

TABLE II d-FEN DOSE DEPENDENTLY AFFECTS THE CYTOTOXICITY OF HUMAN PBMC AGAINST HUMAN LYMPHOMA TUMOR CELLS (K562) In Vitro

| d-FEN Dose (ng/ml) | Percent Change in Cytotoxicity (Mean ± SEM) |
|---|---|
| 0.25 | 19 ± 2 |
| 0.50 | 28 ± 4 |
| 1.00 | 16 ± 3 |
| 4.00 | 11 ± 5 |
| 20.00 | −33 ± 5* |
| 50.00 | −53 ± 6* |
| 100.00 | −87 ± 2* |

*Significantly (p < 0.05) less than all lower doses. One way ANOVA followed by Student's Newman-Keuls All Pairwise Comparison Test.

TABLE III

LOW DOSES OF d-FEN AND d-norFEN PRODUCE EQUIVALENT INCREASES IN THE CYTOTOXIC EFFECTS OF HUMAN PBMC AGAINST HUMAN LYMPHOMA TUMOR CELLS (K562) In Vitro

|  | DONOR #1 | DONOR #2 |
|---|---|---|
| d-FEN (ng/ml) | | |
| 0.25 | 22 | 19 |
| 0.50 | 36 | 21 |
| 1.00 | 23 | 17 |
| d-norFEN (ng/ml) | | |
| 0.25 | 29 | 19 |
| 0.50 | 24 | 28 |
| 1.00 | 11 | 13 |

Data presented as the percent increase in cytotoxicity produced by each of the three doses of d-FEN and d-norFEN on PBMC obtained from two human donors.

EXAMPLE A

Pharmaceutical composition

A typical formula for 1,000 tablets each containing 5 mg of dextrofenfluramine is as follows:

| Dextrofenfluramine | 5 g |
|---|---|
| Hydroxypropyl cellulose | 2 g |
| Wheat starch | 10 g |
| Lactose | 105 g |
| Magnesium stearate | 3 g |
| Talc | 3 g |

OPERATION

Mode of Administration

The pharmaceutical compositions of the present invention contain dextrofenfluramine or a pharmaceutically-acceptable acid addition salt thereof, preferably in combination with a usual carrier or diluent, and the pharmaceutical form employed, although preferably suitable for administration by the oral route, may take other pharmaceutical forms such as those for parenteral, transcutaneous, nasal, rectal, or perlingual administration, and most especially in the form of tablets, sublingual tablets, glossettes, hard gelatin capsules, capsules, lozenges, suppositories, creams, ointments, skin gels, or the like.

It is therefore seen that a method for the treatment of a human for the enhancement of lymphocyte activity against opportunistic microbial pathogens or against tumors comprising the step of administering to a living human in need thereof of a lymphocyte-activity-enhancing amount of dextrofenfluramine or a pharmaceutically-acceptable acid addition salt thereof, the human treated for enhancement of lymphocyte activity against tumors being any human and the method of treating a human for the enhancement of lymphocyte activity against opportunistic microbial pathogens being an immunocompromised human, illustratively immunocompromised by HIV positive or AIDS, has been provided and whereby all of the other objects of the invention as hereinbefore stated have been achieved.

It is to be understood that the present invention is not to be limited to the exact details of operation, or to the exact compounds, compositions, methods, procedures, or embodiments shown and described, as various modifications and equivalents will be apparent to one skilled in the art, wherefore the present invention is to be limited only by the full scope which can be legally accorded to the appended claims.

We claim:

1. A method for the treatment of an immunocompromised human for the enhancement of lymphocyte activity against opportunistic microbial pathogens comprising the step of orally administering to a living immunocompromised human in need thereof a lymphocyte-activity-enhancing amount of dextrofenfluramine or a pharmaceutically-acceptable acid addition salt thereof, the dextrofenfluramine or pharmaceutically-acceptable acid addition salt thereof being administered in an amount which provides a plasma level of dextrofenfluramine and dextronorfenfluramine between about 1 and about 20 ng/ml.

2. A method of claim 1 wherein the dextrofenfluramine is orally administered together with a pharmaceutically-acceptable carrier or diluent.

3. A method of claim 1 wherein the dextrofenfluramine is administered in amount up to about 9 mg/day.

4. A method of claim 3 wherein the dosage of the dextrofenfluramine ranges from about 1 to about 9 mg per day.

5. A method of claim 1 wherein the human is immunocompromised by HIV positive.

6. A method of claim 5 wherein the human is an HIV positive human suffering from AIDS.

7. A method of claim 1 wherein the enhancement is the enhancement of the activity of human peripheral blood lymphocytes.

8. A method of claim 1 wherein the opportunistic microbial pathogen is a fungus.

9. A method of claim 8 wherein the opportunistic microbial pathogen is a *Candida albicans* fungus.

10. A method of claim 1 wherein the lymphocytes are activated by administration of a lymphocyte activator prior to administration of the dextrofenfluramine.

11. A method of claim 10 wherein the lymphocytes are activated by administration of IL-2 (interleukin-2).

* * * * *

UNITED STATES PATENT AND TRADEMARK OFFICE
CERTIFICATE OF CORRECTION

PATENT NO. : 5,955,508
DATED : September 21, 1999
INVENTOR(S) : Stanley A. Lorens, H.L. Matthews, J. Clancy, Jr., J. Goral, B. Riveline It is certified that error appears in the above-identified patent and that said Letters Patent is hereby corrected as shown below:

Column 16, line 62(approx.): "Den" should read -- d-FEN --.

Column 18, line 9: "$1x10^5$" should read -- $1x10^6$ --.

Signed and Sealed this

First Day of August, 2000

Attest:

Q. TODD DICKINSON

*Attesting Officer*  *Director of Patents and Trademarks*